US008003091B2

(12) United States Patent
Brahmbhatt et al.

(10) Patent No.: US 8,003,091 B2
(45) Date of Patent: Aug. 23, 2011

(54) PHARMACEUTICAL COMPOSITIONS COMPRISING PURIFIED INTACT BACTERIAL MINICELLS

(75) Inventors: Himanshu Brahmbhatt, Sydney (AU); Jennifer MacDiarmid, Sydney (AU)

(73) Assignee: Engeneic Molecular Delivery Pty. Ltd., North Ryde NSW (AU)

( * ) Notice: Subject to any disclaimer, the term of this patent is extended or adjusted under 35 U.S.C. 154(b) by 113 days.

(21) Appl. No.: 11/691,698

(22) Filed: Mar. 27, 2007

(65) Prior Publication Data
US 2007/0241067 A1 Oct. 18, 2007

Related U.S. Application Data

(62) Division of application No. 10/602,021, filed on Jun. 24, 2003, now Pat. No. 7,611,885.

(51) Int. Cl.
*C12N 1/12* (2006.01)
*C12N 1/00* (2006.01)

(52) U.S. Cl. .... 424/93.4; 435/243; 435/244; 435/252.1; 435/261; 435/252.8

(58) Field of Classification Search .......................... None
See application file for complete search history.

(56) References Cited

U.S. PATENT DOCUMENTS

| 6,635,448 | B2 | 10/2003 | Bucciarelli et al. | |
|---|---|---|---|---|
| 7,011,946 | B2 | 3/2006 | Raychaudhuri et al. | |
| 7,125,679 | B2 * | 10/2006 | Ashkar | 435/7.2 |
| 7,183,105 | B2 | 2/2007 | Sabbadini et al. | |
| 2004/0265994 | A1 | 12/2004 | Brahmbhatt et al. | |
| 2007/0237744 | A1 | 10/2007 | Brahmbhatt et al. | |
| 2007/0298056 | A1 | 12/2007 | Brahmbhatt et al. | |
| 2008/0038296 | A1 | 2/2008 | Brahmbhatt et al. | |
| 2008/0051469 | A1 | 2/2008 | Brahmbhatt et al. | |
| 2008/0299084 | A1 | 12/2008 | Brahmbhatt et al. | |

FOREIGN PATENT DOCUMENTS

| WO | WO-00/63364 A2 | 10/2000 |
|---|---|---|
| WO | WO 03/033519 A2 | 4/2003 |
| WO | WO-2005/056749 A2 | 6/2005 |
| WO | WO-2006/066048 A2 | 6/2006 |

OTHER PUBLICATIONS

Brahmbhatt, Cloning and Molecular Characterization of the rfb Gene Cluster from *Salmonella typhimurium* LT2, Thesis, University of Adelaide, S. Australia, Jul. 1987.
Britton et al., "Characterization of a prokaryotic SMC protein involved in chromosome partitioning," Genes Dev., 1998, pp. 1254-1259, vol. 12, Cold Spring Harbor Laboratory Press.
Clark-Curtiss et al., Analysis of Recombinant DNA Using *Escherichia coli* Minicells, Methods in Enzymology, 1983, pp. 347-363, vol. 101, Academic Press, NYC, USA.
De Boer et al., Roles of MinC and MinD in the site-Specific Septation Block Mediated by the MinCDE System of *Escherichia coli*; Journal of Bacteriology, Jan. 1992, pp. 63-70, vol. 174, No. 1, American Society for Microbiology.
Dorward et al., Export and Intercellular Transfer of DNA via Membrane Blebs of *Neisseria gonorrhoeae*, Journal of Bacteriology, May 1989, pp. 2499-2505, vol. 171, No. 5, American Society for Microbiology.
Forbes, Crossflow Microfiltration, Australian Journal of Biotechnology, Jun. 1987, pp. 30-33, vol. 1, No. 1, National Library of Medicine.
Frazer et al., Production, Properties and Utility of Bacterial Minicells, Current Topics in Microbiology and Immunology, 1975, pp. 1-84, 69: 1, National Library of Medicine.
Harlow et al., Cloning and Characterization of the *gsk* Gene Encoding Guanosine Kinase of *Escherichia coli*, Journal of Bacteriology, Apr. 1995, pp. 2236-2240, vol. 177, No. 8, American Society for Microbiology.
Harry, Bacterial cell division: regulating Z-ring formation, Molecular Microbiology, 2001, pp. 795-803, vol. 40(4), Blackwell Science Ltd.
Hiraga et al., Chromosome Partitioning in *Escherichia coli* Novel Mutants Producing Anucleate Cells, Journal of Bacteriology, Mar. 1989, pp. 1496-1505, vol. 171, No. 3, American Society for Microbiology.
Hu et al., Topological regulation of cell division in *Escherichia coli* involves rapid pole to pole oscillation of the division inhibitor MinC under the control of MinD and MinE, Molecular Microbiology, 1999, pp. 82-90, vol. 34(1), Blackwell Science Ltd.
Ireton et al., *spoOI* Is Required for Normal Chromosome Segregation as well as the Initiation of Sporulation in *Bacillus subtilis*, Journal of Bacteriology, Sep. 1994, pp. 5320-5329, vol. 176, No. 17, American Society for Microbiology.
Katsui et al., Heat-Induced Blebbing and Vesiculation of the Outer Membrane of *Escherichia coli*, Journal of Bacteriology, Sep. 1982, pp. 1523-1531, vol. 151, No. 3, American Society for Microbiology.
Kihara et al., Analysis of a FLiM-FliN Flagellar Switch Fusion Mutant of *Salmonella typhimurium*, Journal of Bacteriology, Aug. 1996, pp. 4582-4589, vol. 178, No. 15, American Society for Microbiology.
Levin et al., Identification of *Bacillus subtilis* Genes for Septum Placement and Shape Determination, Journal of Bacteriology, Nov. 1992, pp. 6717-6728, vol. 174, No. 21, American Society for Microbiology.
Matsuzaki et al., Interactions of an antimicrobial peptide, magainin 2, with outer and inner membranes of Gram-negative bacteria, BBA, 1997, pp. 119-130, vol. 1327, Elsevier Science B.V.

(Continued)

*Primary Examiner* — Leon B Lankford
(74) *Attorney, Agent, or Firm* — Stephen A. Bent; Foley & Lardner LLP

(57) ABSTRACT

The present invention provides a method for purifying bacterial minicells that involves subjecting a sample containing minicells to density gradient centrifugation in a biologically compatible medium. The method optionally includes a preliminary differential centrifugation step and one or more filtration steps. The invention also provides a method for purifying bacterial minicells in which a sample containing minicells is subjected to a condition that induces parent bacterial cells to adopt a filamentous form, followed by filtration of the sample to separate minicells from parent bacterial cells. The inventive methods optionally include one or more steps to remove endotoxin from purified minicell preparations, and/or treatment of purified minicell preparations with an antibiotic. Additionally, the invention provides purified minicell preparations, prepared according to the foregoing methods, and containing fewer than about 1 contaminating parent bacterial cell per $10^7$, $10^8$, $10^9$, $10^{10}$, or $10^{11}$ minicells.

13 Claims, 7 Drawing Sheets

OTHER PUBLICATIONS

Okada et al., Possible function of the cytoplasmic axial filaments in chromosomal segregation and cellular division of *Escherichia coli*, Science Progress, 1993/94, pp. 253-264, vol. 77(3/4).

Okada et al., Cytoplasmic Axial Filaments in *Escherichia coli* Cells: Possible Function in the Mechanism of Chromosome Segregation and Cell Division, Journal of Bacteriology, Feb. 1994, pp. 917-922, vol. 176, No. 3, American Society for Microbiology.

Raskin et al., MinDE-Dependent Pole-to-Pole Oscillation of Division Inhibitor MinC in *Escherichia coli*, Journal of Bacteriology, Oct. 1999, pp. 6419-6424, vol. 181, No. 20, American Society for Microbiology.

Reeve, Use of Minicells for Bacteriophage-Directed Polypeptide Synthesis, Methods in Enzymology, 1979, pp. 493-503, vol. 68, Academic Press, NYC, USA.

Reeve et al., Bacteriophage SPO1-Induced Macromolecular Synthesis in Minicells of *Bacillus subtilis*, Journal of Bacteriology, Jun. 1975, pp. 1308-1316, vol. 15, No. 6, American Society for Microbiology.

Sancar et al., Simple Method for Identification of Plasmid-Coded Proteins, Journal of Bacteriology, Jan. 1979, pp. 692-693, vol. 137, No. 1.

Stewart et al., Genetic and Morphological Characterization of an *Escherichia coli* Chromosome Segregation Mutant, Journal of Bacteriology, Jul. 1992, pp. 4513-4516, vol. 174, No. 13, American Society for Microbiology.

Wachi et al., New *mre* Genes *mreC* and *mreD*, Responsible for Formation of the Rod Shape of *Escherichia coli* Cells, Journal of Bacteriology, Dec. 1989, pp. 6511-6516, vol. 171, No. 12, American Society for Microbiology.

Alice A. Christen et al., "Rapid isolation of *Escherichia coli* minicells by glass-fiber filtration: study of plasmid-coded polypeptides", Gene 23, (1983) pp. 195-198.

H. Stieglitz et al., "Cloning, Sequencing, and Expression in Ficoll-Generated Minicells of an *Escherichia coli* Heat-Stable Enterotoxin Gene", Plasmid 20, 42-53 (1988).

George G. Khachatourians et al., "A New Method for the Preparation of Minicells for Physiological Studies", Preparative Biochemistry, 3(3), 291-298 (1973).

George G. Khachatourians et al., "Expression of Recombinant DNA Functional Products in *Escherichia coli* Anucleate Minicells", Biotech. Adv. vol. 4 pp. 75-93, 1986.

Alan Bridge et al., "Induction of an interferon response by RNAi vectors in mammalian cells," Nature Genetics, vol. 34, No. 3, (2003), pp. 263-264.

Catherine Grillot-Courvalin et al., "Wild-type intracellular bacteria delivery DNA into mammalian cells," Cellular Microbiology, vol. 4, No. 3, (2002), pp. 177-186.

Dawn E. Colwell et al., "Monoclonal Antibodies to Salmonella Lipopolysaccharide: Anti-O-Polysaccharide Antibodies Protect C3H Mice Against Challenge with Virulent *Salmonella typhimurium*," The Journal of Immunology, vol. 133, No. 2, Aug. 1984, pp. 950-957.

H. Brahmbhatt et al., U.S. PTO Office Action, U.S. Appl. No. 10/581,990 dated Mar. 19, 2009, 32 pgs.

H. Brahmbhatt et al., U.S. PTO Office Action, U.S. Appl. No. 10/588,028 dated Mar. 18, 2009, 23 pgs.

H. Brahmbhatt et al., U.S. PTO Office Action, U.S. Appl. No. 10/602,021 dated May 4, 2006, 10 pgs.

H. Brahmbhatt et al., U.S. PTO Office Action, U.S. Appl. No. 10/602,021 dated May 15, 2007, 10 pgs.

H. Brahmbhatt et al., U.S. PTO Office Action, U.S. Appl. No. 10/602,021 dated Jul. 25, 2008, 10 pgs.

H. Brahmbhatt et al., U.S. PTO Office Action, U.S. Appl. No. 11/211,098 dated Feb. 24, 2009, 24 pgs.

H. Brahmbhatt et al., U.S. PTO Office Action, U.S. Appl. No. 11/211,098 dated Apr. 24, 2008, 38 pgs.

H. Brahmbhatt et al., U.S. PTO Office Action, U.S. Appl. No. 11/211,098 dated Aug. 7, 2009, 23 pgs.

H. Brahmbhatt et al., U.S. PTO Office Action, U.S. Appl. No. 11/765,635 dated Oct. 6, 2009, 40 pgs.

H. Brahmbhatt et al., U.S. PTO Office Action, U.S. Appl. No. 12/053,197 dated Aug. 25, 2009, 25 pgs.

Hao Wu et al., "Small Interfering RNA-induced Suppression of MDRI (P-Glycoprotein) Restores Sensitivity to Multidrug-resistant Cancer Cells," Cancer Research, vol. 63, Apr. 1, 2003, pp. 1515-1519.

Ian Tomlinson et al., "Methods for Generating Multivalent and Bispecific Antibody Fragments," Methods in Enzymology, vol. 326, (2000), pp. 461-479.

Inder M. Verma et al., "Gene Therapy: Twenty-First Century Medicine," Annu. Rev. Biochem., vol. 74, (2005), pp. 711-738.

J. H. Hong et al., "Antisense Bcl2 oligonucleotide in cisplatin-resistant bladder cancer cell lines," BJU International, vol. 90, (2002), pp. 113-117.

Jean-Remi Bertrand et al., "Comparison of antisense oligonucleotides and siRNAS in cell culture and in vivo," Biochemical and Biophysical Research Communications, vol. 296, (2002), pp. 1000-1004.

L. R. Kelland, "Of mice and men: values and liabilities of the athymic nude mouse model in anticancer drug development," European Journal of Cancer, vol. 40, (2004), pp. 827-836.

Leoni A. Kunz-Schughart et al., "The Use of 3-D Cultures for High-Throughput Screening: The Multicellular Spheriod Model," Journal of Biomolecular Screening, vol. 9, (2004), pp. 273-285.

Michael J. McCluskie et al., "Route and Method of Delivery of DNA Vaccine Influence Immune Responses in Mice and Non-Human Primates," Molecular Medicine, vol. 5, (1999), pp. 287-300.

Michele Carbone et al., "Multistep and multifactorial carcinogenesis: when does a contributing factor become a carcinogen?," Seminars in Cancer Biology, vol. 14, (2004) pp. 399-405.

Michele De Palma et al., "In Vivo Targeting of Tumor Endothelial Cells by Systemic Delivery of Lentiviral Vectors," Human Gene Therapy, vol. 14, Aug. 10, 2003, pp. 1193-1206.

Robert S. Kerbel, "What is the optimal rodent model for anti-tumor drug testing?," Cancer and Metastasis Reviews, vol. 17, (1999), pp. 301-304.

Stephen L. Eck et al., "Gene-Based Therapy," Chapter 5, Goodman & Gilman's The Pharmacological Basis of Therapeutics, (1996), pp. 77-102.

Yi Lu et al., "Delivery of adenoviral vectors to the prostate for gene therapy," Cancer Gene Therapy, vol. 6, No. 1, (1999), pp. 64-72.

Notice of Allowance U.S. Appl. No. 10/602,021 dated Jun. 22, 2009.

Letter from Knobbe Martens Olson & Bear LLP dated Feb. 26, 2010.

Aline Jaffe et al., "Minicell-Forming Mutants of *Escherichia coli*: Production of Minicells and Anucleate Rods", Journal of Bacteriology, vol. 170, No. 7, Jul. 1988, pp. 3094-3101.

Thomas L. Hale et al., "Characterization of Virulence Plasmids and Plasmid-Associated Outer Membrane Proteins in *Shigella flexneri, Shigella sonnei,* and *Escherichia coli*", Infection and Immunity, Apr. 1983, vol. 40, No. 1, pp. 340-350.

Manisha P. Desai et al., "The Mechanism of Uptake of Biodegradable Micropartiles in Caco-2 Cells Is Size Dependent", Pharmaceutical Research, vol. 14, No. 11, 1997, pp. 1568-1573.

Igor Dmitriev et al., "Ectodomain of Coxsackievirus and Adenovirus Receptor Genetically Fused to Epidermal Growth factor Mediates Adenovirus Targeting to Epidermal Growth Factor Receptor-Positive Cells", Journal of Virology, Aug. 2000, vol. 74, No. 15, pp. 6875-6884.

Chrostoph Mamot et al., "Epidermal Growth Factor Receptor (EGFR)-targeted Immunoliposomes Mediate Specific and Efficient Drug Delivery to EGFR- and EGFRvIII-overexpressing Tumor Cells", Cancer Research 63, Jun. 15, 2003, pp. 3154-3161.

William F. Scherer M.D. et al., "The Viral Range in Vitro of a Malignant Human Epithelial Cell (Starin Hela, Gey)—III. Studies With Pseudolymphocytic Choriomeningitis Virus General Discussion", pp. 31-39.

Masahiro Watarai et al., "Interaction of Ipa Proteins of *Shigella flexneri* with α5β1 Integrin Promotes Entry of the Bacteria into Mammalian Cells", J. Exp. Med. @ The Rockefeller University Press, vol. 183, Mar. 1996, pp. 991-999.

Tibor Pal et al.,"Plasmid-Associated Adherence of *Shigella flexneri* in a HeLa Cell Mode", Infection and Immunity, Aug. 1989, vol. 57, No. 8, pp. 2580-2582.

William F. Scherer M.D. et al., "Studies on the Propagation in Vitro of Poliomyelitis Viruses-IV. Viral Multiplication in a Stable Strain of Human Malignant Epithelial Cells (Strain HeLa) Derived from an Epidermoid Carcinoma of the Cervix", The Journal of Experimental Medicine vol. 97, Jan. 20, 1953, pp. 695-715.

Jagath L. Kadurugamuwa et al., "Virulence Factors Are Released from *Pseudomonas aeruginosa* in Association with Membrane Vesicles during Normal Growth and Exposure to Gentamicin: a Novel Mechanism of Enzyme Secretion", Journal of Bacteriology, Jul. 1995, vol. 177, No. 14, pp. 3998-4008.

Final Office Action U.S. Appl. No. 12/019,090 Dated Sep. 15, 2010.

* cited by examiner

FIG. 1A

Minicell purification procedure without the inventive techniques

Overnight culture of minicell producing bacterial cells

Differential centrifugation @ 2000g 20 min
*Pellet most bacterial cells while minicells remain
In supernatant*

First Cross-flow filtration through 0.45 μm filter
*Reduce parent bacterial cell contamination
minicells are 0.4um diameter and filter through
but Some loss of minicells*

Second Cross-flow filtration through 0.45 μm filter
*Further reduce parent bacterial cell contamination.
Some loss of minicells.*

Replace with → To FIG. 1B

Cross-flow filtration through 0.2 μm filter
*Retain minicells but eliminate all contaminants
smaller than 0.2 um in size*

Cross-flow filtration through 0.1μm filter
*Concentrate minicells*

Dead-end filtration through 0.45 μm filter       From FIG.1B
*Eliminate most of the residual parent
bacterial cells*

Concentrate minicells through 100kDa filter

To FIG.1B 000015  3KV  X45.0K  670nm 000020  2KV  X70.0K  430nm 010005  3KV  X60.0K  500nm

*S. Typhimurium* parent →
Bacterial cells (solid arrow)

Minicells (dashed arrow) ⇢

000015  3KV  X10.0K  0.00um

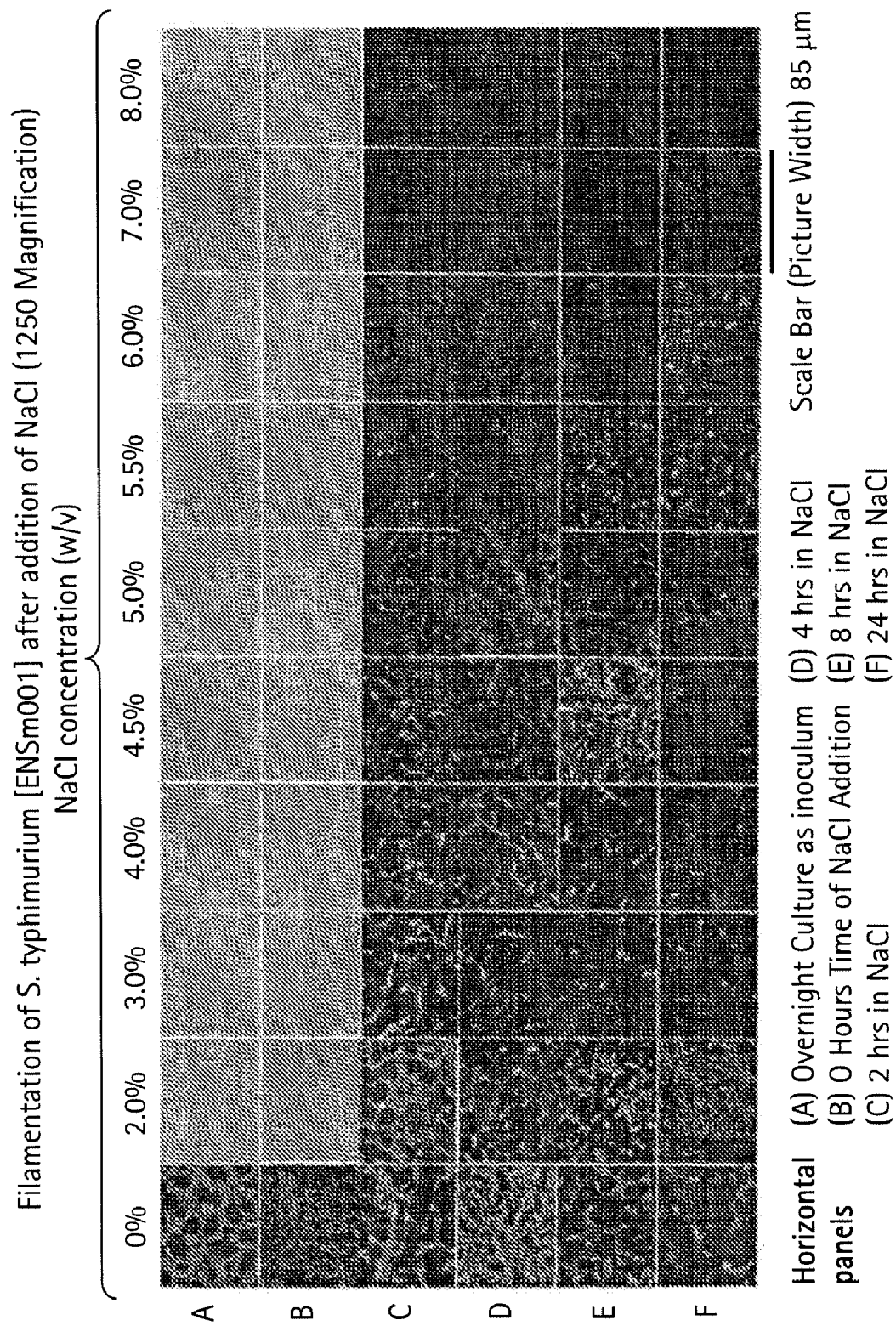

Salt induced Filamentation in *Salmonella typhimurium* ENSm026

4 hours after Log Culture Inoculum (0% NaCl)

4 hours after Log Culture Inoculum (5.0% NaCl)

Scale Bar 50 μm)

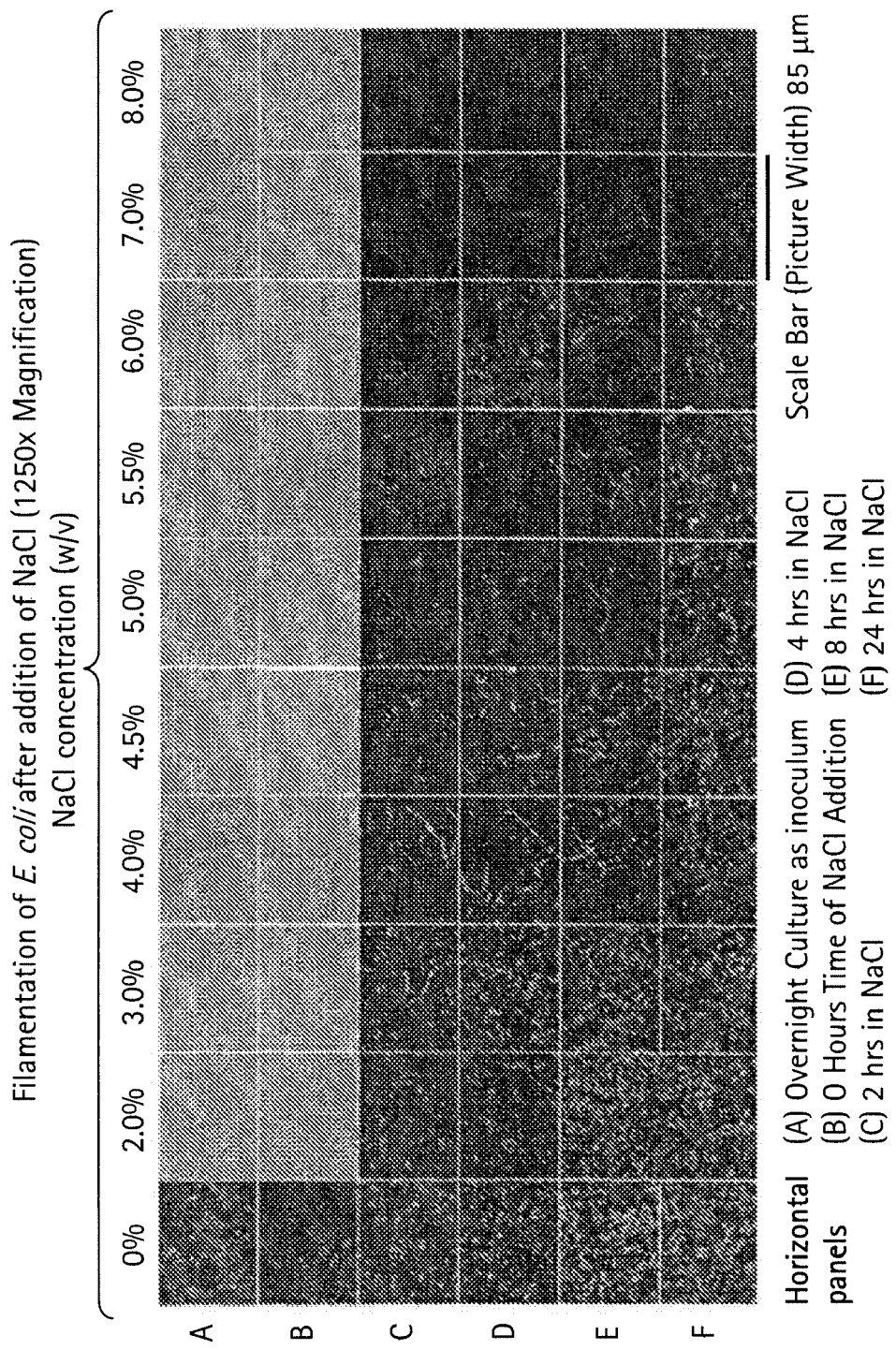

Salt induced Filamentation in *E. coli*

4 hours after Log Culture Inoculum (0% NaCl)

4 hours after Log Culture Inoculum (5.0% NaCl)

Scale Bar 50 μm)

PHARMACEUTICAL COMPOSITIONS COMPRISING PURIFIED INTACT BACTERIAL MINICELLS

BACKGROUND OF THE INVENTION

The present invention relates to a pharmaceutically compatible method for purifying intact bacterial minicells.

A minicell is an anucleate form of an *E. coli* or other bacterial cell, engendered by a disturbance in the coordination, during binary fission, of cell division with DNA segregation. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an anulceate minicell (de Boer et al., 1992; Raskin & de Boer, 1999; Hu & Lutkenhaus, 1999; Harry, 2001).

In addition to min operon mutations, anucleate minicells also are generated following a range of other genetic rearrangements or mutations that affect septum formation, for example in the divIVB1 in *B. subtilis* (Reeve and Cornett, 1975; Levin et al., 1992). Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation, for example the smc mutation in *Bacillus subtilis* (Britton et al., 1998), spoOJ deletion in *B. subtilis* (Ireton et al., 1994), mukB mutation in *E. coli* (Hiraga et al., 1989), and parC mutation in *E. coli* (Stewart and D'Ari, 1992). Gene products may be supplied in trans. When over-expressed from a high-copy number plasmid, for example, CafA may enhance the rate of cell division and/or inhibit chromosome partitioning after replication (Okada et al., 1994), resulting in formation of chained cells and anucleate minicells (Wachi et al., 1989; Okada et al., 1993).

Minicells are distinct from other small vesicles that are generated and released spontaneously in certain situations and, in contrast to minicells, are not due to specific genetic rearrangements or episomal gene expression. Exemplary of such other vesicles are bacterial blebs, which are small membrane vesicles (Dorward et al., 1989). Blebs have been observed in several bacterial species from *Agrobacterium, Bacillus, Bordetella, Escherichia, Neisseria, Pseudomonas, Salmonella* and *Shigella*, for example. Bacterial blebs can be produced, for instance, through manipulation of the growth environment (Katsui et al., 1982) and through the use of exogenous membrane-destabilizing agents (Matsuzaki et al., 1997).

Because plasmid replication within prokaryotic cells is independent of chromosomal replication, plasmids can segregate into both normal daughter cells and minicells during the aberrant cell division described above. Thus, minicells derived from recombinant min *E. coli* carry significant numbers of plasmid copies, with all of the bacterial cellular components except for chromosomes, and have been used as such in studying plasmid-encoded gene expression in vitro. See Brahmbhatt (1987), Harlow et al. (1995), and Kihara et al. (1996). Brahmbhatt (1987) demonstrated, for example, that *E. coli* minicells can carry recombinant plasmids with DNA inserts as large as 20 kb, absent any chromosomal DNA, and can express nine or more recombinant proteins simultaneously.

A recent patent application, PCT/IB02/04632 (incorporated entirely herein by reference), described recombinant, intact minicells containing therapeutic nucleic acid molecules. Such minicells are effective vectors for delivering oligonucleotides and polynucleotides to host cells in vitro and in vivo. Accordingly, they are particularly useful for introducing nucleic acid molecules that, upon transcription and/or translation, function to ameliorate or otherwise treat a disease or modify a trait associated with a particular cell type, tissue or organ of a subject.

In vivo minicell applications generally require minicell preparations of a high purity, particularly with respect to live parent bacteria, free endotoxin and cellular debris (including membrane fragments, nucleic acids and intracellular components) that might elicit an inflammatory response in an immunized host. Moreover, the use of minicells in commercial pharmaceutical products will require methods for purifying minicells to approved international pharmaceutical standards. To this end, conventional methods of minicell purification generally are unsatisfactory.

Conventional techniques entail (a) low speed centrifugation, to reduce the bio-burden of parent cells, and (b) differential rate sedimentation in a gradient of glycerol, sucrose or percoll. An initial differential, low speed centrifugation typically reduces parental cells by as much as 100-fold, while leaving 50% to 70% of minicells in the supernatant fluid. Two subsequent cycles of differential rate sedimentation then yield minicell preparations having a purity of about 1 vegetative cell per $10^6$-$10^7$ minicells. Such conventional methods are reviewed by Frazer & Curtiss (1975), and are described by Reeve (1979), Clark-Curtiss & Curtiss (1983), and U.S. Pat. No. 4,311,797 (to Khachatourians).

The purity achieved by conventional purification methods may not be adequate for all in vivo applications, some of which may require doses greater than $10^6$ minicells, or even $10^{10}$ minicells. At the aforementioned contamination ratio, this would translate into 10,000 live parent cells per dose. Such a contamination level could be fatal, particularly in immuno-compromised patients such as cancer and AIDS patients. For example, the $ID_{50}$ (infectious dose in 50% of infected people) for *Shigella dysenteriae, Salmonella enteritidis* and *Listeria monocytogenes* organisms is approximately 10, 1,000 and 10 respectively. Moreover, previous studies have reported that the level of parental cell contamination varies with different bacterial strains (Clarke-Curtiss and Curtiss, 1983). In that regard, gene therapy applications described in PCT/IB02/04632 may employ minicells derived from a range of mutant Gram-negative and Gram-positive bacterial strains, and would require minicells that are essentially free of live parent bacterial cell contamination. Thus, conventional minicell purification methods do not permit quality control for cGMP (current good manufacturing practice) manufacture of biopharmaceutical doses of minicells.

As an additional drawback, the gradient formation media (percoll, sucrose and glycerol) employed by conventional purification methods are incompatible with in vivo uses. Percoll is toxic and, hence, is restricted to "research purposes only" contexts. Sucrose imparts a high osmolarity to gradients that can cause physiological changes in minicells. Indeed, the present inventors have determined that minicells undergo an osmotic shock in sucrose gradients and, as a consequence, become structurally deformed. Glycerol is highly viscous and difficult to remove completely from the minicell suspensions. Accordingly, although these density gradient media effectively separate cells and cellular organelles or components, they are not suitable for separating biological cells that are destined for clinical use in humans.

Several approaches have been developed to improve conventional minicell purification techniques. One approach employs parent cells that carry a chromosomal recA mutation, and treatment with low doses of Ultra Violet (UV) radiation (Sancar et al., 1979). The rationale of this approach is that UV radiation will preferentially degrade chromosomal DNA because of its large target size, as opposed to smaller plasmid DNA. However, recombinant minicells used for gene therapy and vaccine applications must be free of any mutation, and non-specific mutagenesis methods such as UV radiation would not ensure that all plasmid DNAs remain un-mutated.

Another approach to improve minicell purification operates by inhibiting bacterial cell wall synthesis, such as by using ampicillin or cycloserine, or by starving diaminopimelic acid (DAP)-requiring strains of DAP (Clarke-Curtiss and Curtiss, 1983). This approach also suffers from several drawbacks, however. First, many recombinant plasmids used for gene therapy will carry an ampicillin resistance marker, which renders parent cells carrying the plasmid ampicillin resistant. Second, many in-vivo minicell applications will employ minicells derived from a range of different bacterial species, many of which may not be susceptible to DAP-requiring mutations. Third, any large-scale use of antibiotics is undesirable due to the attendant risks of generating antibiotic-resistant bacteria.

Recently, a novel approach for purifying minicells that addresses the above-mentioned concerns was reported (PCT/IB02/04632). The novel method combines cross-flow filtration (feed flow is parallel to a membrane surface; Forbes, 1987) and dead-end filtration (feed flow is perpendicular to the membrane surface) to achieve a minicell purity that exceeds $10^{-7}$ (i.e., fewer than one parent cell per $10^7$ minicells), and even $10^{-9}$. Optionally, the filtration combination can be preceded by a differential centrifugation, at low centrifugal force, to remove some portion of the bacterial cells and thereby enrich the supernatant for minicells.

Although this filtration procedure overcomes the drawbacks associated with conventional minicell purification techniques, it also has limitations. Foremost, cross-flow filtration results in considerable loss of minicells, which adds cost to the manufacturing process. Additionally, minicell preparations obtained by the filtration procedure contain some bacterial endotoxin, which causes a mild shock when administered in vivo. Finally, minicell purity varies from batch to batch when the filtration methods are employed.

Therefore, a need remains for methods of purifying bacterial minicells that maximize minicell yield and purity, while employing biologically compatible media.

To address these and other needs, the present invention provides a method for purifying bacterial minicells that involves subjecting a sample containing minicells to density gradient centrifugation in a biologically compatible medium. The method optionally includes a preliminary differential centrifugation step.

The present invention also provides a method for purifying bacterial minicells that combines density gradient centrifugation in a biologically compatible medium with filtration.

In another aspect, the present invention provides a minicell purification method in which a sample containing minicells is subjected to a condition that induces parent bacterial cells to adopt a filamentous form, followed by filtration of the sample to separate minicells from parent bacterial cells.

In yet another aspect, the present invention provides a minicell purification method that includes (a) subjecting a sample containing minicells to density gradient centrifugation in a biologically compatible medium, (b) subjecting the sample to a condition that induces parent bacterial cells to adopt a filamentous form, then (c) filtering the sample to obtain a purified minicell preparation.

The inventive methods optionally include one or more steps to remove endotoxin from purified minicell preparations, and/or treatment of purified minicell preparations with an antibiotic.

Finally, the present invention provides purified minicell preparations, prepared according to the foregoing methods, and containing fewer than about 1 contaminating parent bacterial cell per $10^7$, $10^8$, $10^9$, $10^{10}$ or $10^{11}$ minicells

BRIEF DESCRIPTION OF THE DRAWINGS

FIG. 3A shows the filamentation of parent S. typhimurium minCDE-strain bacteria following incubation with various NaCl concentrations for various times.

FIG. 4A shows the filamentation of parent E. coli minCDE-strain bacteria following incubation with various NaCl concentrations for various times.

DETAILED DESCRIPTION OF PREFERRED EMBODIMENTS

Figure 1B:
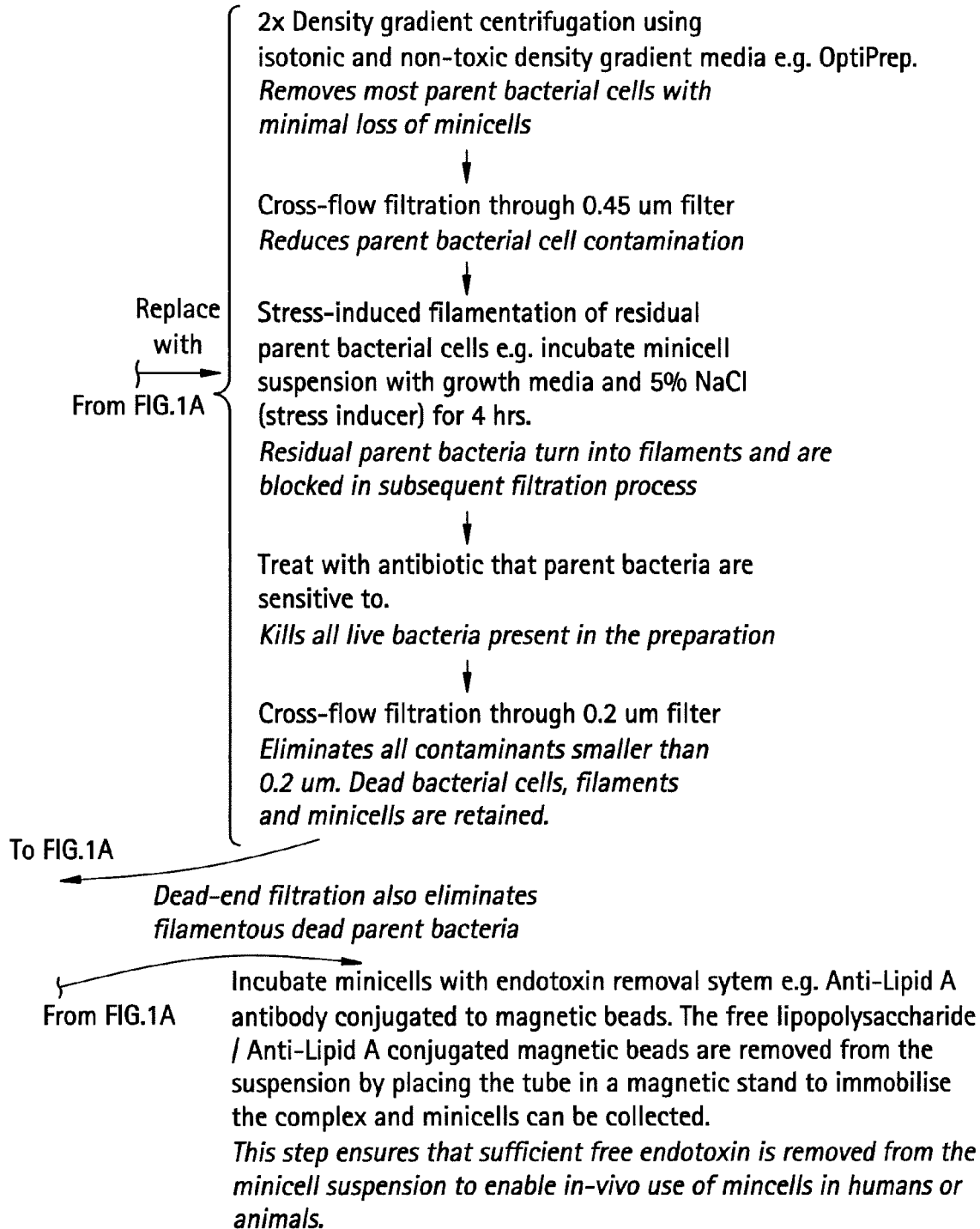
FIG. 1 depicts one way in which minicell purification techniques of the present invention can be integrated with other minicell purification procedures.
Figure 2A:
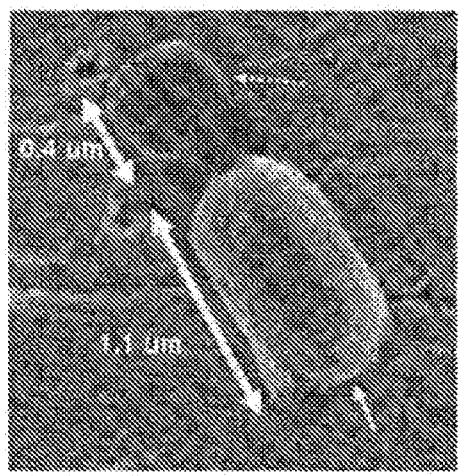
FIG. 2 shows Scanning Electron Micrographs of S. typhimurium minCDE-strain bacteria (range of different sizes) and minicells derived from the strain. (A) shows a small sized parent bacterium (1.1 um long) and a minicell (0.4 um diameter), (B) shows a larger parent bacterium (1.32 um long), (C) shows an even larger parent bacterium (1.6 um long), and (D) shows a mixture of parent bacteria and minicells, where the former range in length from 1 um to 4 um.
Figure 2B:
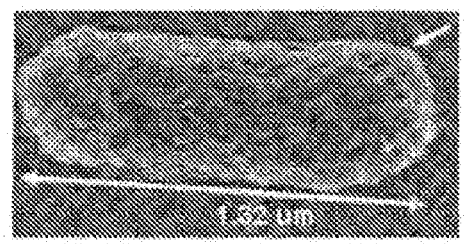
Figure 2C:
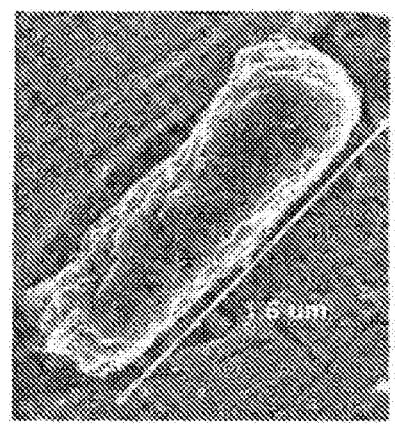
Figure 2D:
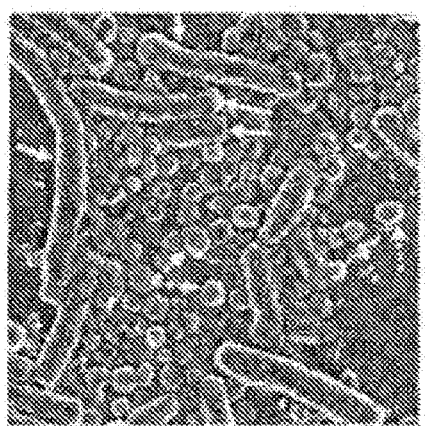

The present inventors have determined that the use of biologically compatible media improves conventional minicell purification. In this regard, they have observed that commonly used density gradient media, while effective at separating minicells from contaminants, often have adverse effects on minicells. For example, conventional methods commonly employ 30% sucrose gradients and require two to three repeated sucrose gradient purifications to achieve adequate purity. This exposes minicells to high osmotic pressure for up to two hours, likely causing osmotic shock to the minicells. The present inventors have found that sucrose-gradient purified minicells often are significantly deformed relative to minicells purified by other means. Presumably, the deformity results from membrane destabilization, which allows excess fluid into the minicells. Such membrane destabilization, and its attendant increase in membrane porosity, also could allow cytosol contents, including therapeutic nucleic acids to leak out of the minicells.

In one aspect, therefore, the present invention contemplates a minicell purification method that comprises separating minicells from parent bacterial cells and other contaminants via density gradient centrifugation in a biologically compatible medium. After centrifugation, a minicell band is collected from the gradient, and, optionally, the minicells may be subjected to further rounds of density gradient centrifugation to maximize purity. The method may further include a preliminary step of performing differential centrifugation on the minicell-containing sample. When performed at low centrifugal force, differential centrifugation will remove some portion of parent bacterial cells, thereby enriching the supernatant for minicells.

"Biologically compatible media," used in this context, refers to media that do not adversely affect minicell physiology or morphology. Preferably, biologically compatible media also do not adversely affect host cell physiology, or host organism physiology. The meaning of "biologically compatible" is therefore contextual. For example, a particular medium may be biologically compatible to one type of minicell, but toxic to another. Preferably biologically compatible media are both isotonic and non-toxic.

OptiPrep™ (Axis-Shield PLC, Dundee, Scotland), which is a sterile 60% (w/v) solution of iodixanol (5,5'-[(2-hydroxy-1-3 propanediyl)-bis(acetylamino)]bis [N,N'-bis(2,3dihydroxypropyl-2,4,6-triiodo-1,3-benzenecarboxamide]) in water, constitutes one highly preferred example of a biologically compatible medium. Researchers have extensively utilized OptiPrep™ and other similar density gradient media for purifying mammalian cells and organelles, as well as membrane vesicles, viruses, proteins, nucleic acids and lipoproteins. These uses are reviewed in *Density Gradient Media. Applications and Products* 2002, Axis-Shield PLC, Dundee, Scotland. Such media were not previously employed, however, to purify bacterially-derived minicells. Indeed, prior to the present inventors' observation that other media adversely affect minicell physiology and morphology, a need for biologically compatible media to purify minicells was not even recognized.

With OptiPrep™ it is possible to use either preformed gradients, or to form a gradient in situ by centrifugation (self-generating gradient). Preformed gradients can be continuous or discontinuous gradients. Preformed gradients of OptiPrep™ can be formed by layering solutions of the desired concentrations into a centrifuge tube and allowing the solutions to diffuse by sealing the top of the tube and laying it on its side during diffusion. The preparation of isoosmotic density gradients with OptiPrep™ depends upon preparing gradient solutions by dilution of OptiPrep™ solution with an appropriate diluent solution. Selection of a diluent solution and osmotic balancers is well within the ordinary skill or practitioners.

In another aspect, the present invention combines density gradient centrifugation in a biologically compatible medium with filtering steps. For example, density gradient centrifugation can be incorporated into a serial filtration process, as exemplified in FIG. 1. One such serial filtration process is described in PCT/IB02/04632. Briefly, that process combines cross-flow filtration (feed flow is parallel to a membrane surface) and dead-end filtration (feed flow is perpendicular to a membrane surface). Optionally, this combination can be preceded by a differential centrifugation, at low centrifugal force, to remove some portion of parent bacterial cells and thereby enrich the supernatant for minicells. Also optionally, the combination can be followed by an antibiotic treatment to kill residual parent bacterial cells.

Cross-flow filtration, depending on the filter pore size, can separate minicells from larger contaminants such as parent bacterial cells, and from smaller contaminants such as bacterial blebs, free endotoxin, nucleic acids, cellular debris and excess liquid. To separate minicells from larger contaminants, the nominal pore size of cross-flow filters should allow minicells to permeate through the filters, but not large bacterial cells. A 0.45 μm pore size is preferred for this purpose because minicells are approximately 0.4 μm in diameter, whilst bacterial cells are larger. To separate minicells from smaller contaminants, the nominal pore size of cross-flow filters should allow smaller contaminants to permeate through the filters, but not minicells. A 0.2 μm pore size is preferred for this purpose because bacterial blebs range in diameter from 0.05 μm to 0.2 μm, and the other smaller contaminants are less than 0.2 μm.

Effective application of cross-flow filtration in this context typically entails at least one step involving a larger pore size, around 0.45 μm, followed by at least one step with a smaller pore size, around 0.2 μm. Between or during serial cross-flow filtration steps, diafiltration may be performed to maximize recovery of minicells. In the diafiltration, volume is held constant and ultrafiltration membranes are used to retain desired particles (minicells, in this case), while undesirable smaller solutes and particles are removed.

The use of cross-flow filtration accommodates suspensions carrying heavy loads of particulate matter, such as bacterial cultures, which may carry loads of $10^{11}$ to $10^{13}$ bacterial and minicell populations per liter of culture. To minimize filter fouling and the consequent loss of minicells, the bacterial/minicell culture may be diluted, preferably 5-fold to 10-fold. Dilutions also permit use of appropriately low pump pressure and flow rate.

To remove residual parent bacterial cells remaining after cross-flow filtration, dead-end filtration may be performed. For this purpose, the use of at least one dead-end filtration, employing a pore size of about 0.45 μm, is preferred.

In one embodiment, a minicell purification method combines density gradient centrifugation through a biologically compatible medium with a filtration step that employs at least one filter with a pore size less than or equal to about 0.2 μm.

In another embodiment, a minicell purification method combines density gradient centrifugation through a biologically compatible medium with a dead-end filtration step employing a filter with a pore size of about 0.45 μm.

The present inventors also have discovered that inducing parent bacterial cells to adopt a filamentous form, prior to filtration, significantly improves minicell purification. Because minicells and parent bacterial cells have the same diameter (average of 0.4 um) some bacterial cells can permeate a filter pore that barely accommodates a minicell (e.g., 0.45 μm cross-flow or dead-end filter pores), even though the length of bacterial cells is at least 1 μm. This occurs when an oblong bacterial cell lodges itself perpendicular to a filter. However, bacterial cell filaments, consisting of bacterial cells joined end-to-end cannot penetrate such filters.

Thus, another aspect of the invention entails inducing contaminating parent bacterial cells to form filaments prior to filtration. This is accomplished by subjecting a minicell suspension to environmental conditions that induce a stress response in parent cells. Such conditions are well known to those skilled in the art, and include anaerobic conditions, nutrient limiting conditions and abnormal osmotic conditions. Hypertonic media are particularly useful for inducing filamentation. In one example, a minicell suspension can be supplemented with Trypticase Soy Broth (growth medium) that contains 5% sodium chloride (stress inducer). Under such stress-inducing conditions, cells fail to fully septate during cell division, and form long bacterial filaments consisting of multiple cells.

Preferred embodiments of the invention exploit bacterial filamentation to increase minicell purity. Thus, in one aspect, the invention provides a minicell purification method that includes the steps of (a) subjecting a sample containing minicells to density gradient centrifugation in a biologically compatible medium, and (b) subjecting the sample containing minicells to a condition that induces parent bacterial cells to adopt a filamentous form, followed by (c) filtering the sample to obtain a purified minicell preparation.

The present inventors have further discovered that the removal of endotoxin improves minicell preparations. In in vivo mouse studies, they observed a mild shock resulting from the use of minicell preparations containing residual endotoxins. Thus, useful minicell preparations preferably are substantially free from endotoxins.

Methods for removing endotoxins are well-known in the art. One exemplary method utilizes magnetic beads (for example, Dynabeads™; Dynal biotech, Oslo, Norway) coated with anti-Lipid A antibodies. Antibody coated magnetic beads can be mixed with a minicell suspension in a tube, and incubated to allow antibody to bind to free lipopolysaccharide (LPS) via its Lipid A portion. The tube carrying the suspension is then placed in a magnetic stand to immobilize the anti-Lipid A-LPS complexed magnetic beads, and the minicells are collected. Multiple cycles of incubation with fresh beads can be performed to achieve the desired level of purity. Monoclonal antibodies that bind to epitopes found in the deep-core polysaccharide part of LPS also are useful for removing free endotoxin. The deep-core polysaccharide part of LPS is not thought to be exposed on bacterial membrane surfaces. Therefore, antibodies directed against this part of LPS should not bind to bacterial cell-bound LPS. Prior to use, such antibodies should be tested to ensure that they do not cross-react with cell-surface exposed components of LPS.

Due to the potential for bacterial endotoxins to cause adverse side effects, preferred minicell purification methods include one or more steps to remove them. Thus, in one aspect, the invention provides a minicell purification method that employs a density gradient centrifugation step in a biologically compatible medium, followed by one or more steps to remove endotoxin from the resulting enriched minicell preparation. More preferably, the method further includes one or more filtration steps, as described above.

The minicell purification techniques described herein may be employed in various combinations to obtain a preparation of a desired purity. Preferred methods include a combination of density gradient centrifugation and filtration. Preferred methods also include stress-induced filamentation of parent bacterial cells followed by filtration, and removal of endotoxin from minicell preparations. One example of a method (schematically depicted in FIG. 1) that employs all of these techniques is as follows:

Step A: Differential centrifugation of a minicell producing bacterial cell culture. This step, which may be performed at 2000 g for about 20 minutes, removes most parent bacterial cells, while leaving minicells in the supernatant.

Step B: Density gradient centrifugation using an isotonic and non-toxic density gradient medium. This step separates minicells from many contaminants, including parent bacterial cells, with minimal loss of minicells. Preferably, this step is repeated within a purification method.

Step C: Cross-flow filtration through a 0.45 μm filter to further reduce parent bacterial cell contamination.

Step D: Stress-induced filamentation of residual parent bacterial cells. This may be accomplished by subjecting the minicell suspension to any of several stress-inducing environmental conditions.

Step E: Antibiotic treatment to kill parent bacterial cells.

Step F: Cross-flow filtration to remove small contaminants, such as membrane blebs, membrane fragments, bacterial debris, nucleic acids, media components and so forth, and to concentrate the minicells. A 0.2 μm filter may be employed to separate minicells from small contaminants, and a 0.1 μm filter may be employed to concentrate minicells.

Step G: Dead-end filtration to eliminate filamentous dead bacterial cells. A 0.45 um filter may be employed for this step.

Step H: Removal of endotoxin from the minicell preparation. Anti-Lipid A coated magnetic beads may be employed for this step.

Those skilled in the art can implement variations of these steps and incorporate additional purification steps, consistent with the principles outlined herein.

The foregoing methods for purifying bacterial minicells provide purified minicell preparations useful for in vivo applications such as those described in PCT/IB02/04632. These preparations contain fewer than about 1 contaminating parent bacterial cell per $10^7$ minicells, preferably fewer than about 1 contaminating parent bacterial cell per $10^8$ minicells, more preferably fewer than about 1 contaminating parent bacterial cell per $10^9$ minicells, even more preferably fewer than about 1 contaminating parent bacterial cell per $10^{10}$ minicells, and yet more preferably fewer than about 1 contaminating parent bacterial cell per $10^{11}$ minicells. Most preferably, any contaminating parent bacterial cells are dead, and these preparations do not contain any live parent bacterial cells. Moreover, these preparations are substantially free of endotoxins.

Reference to the following, illustrative examples will help to provide a more complete understanding of the invention.

Example 1

Inconsistency of Filtration Without the Inventive Techniques

This example illustrates that the use of filtration to purify minicells, without the inventive techniques, can produce inconsistent results.

Minicell-producing mutant bacterial strains of *S. typhimurium*, *E. coli* and *Shigella flexneri* are analyzed by Scanning Electron Microscopy (SEM) to determine the size of the bacterial cells and minicells. For High Resolution Scanning Electron Microscopy the following method is followed. Bacterial cultures are grown in Trypticase Soy Broth (TSB) (BBL brand purchased from Bacto Labs, Liverpool, NSW, Australia). The broth is prepared according to the manufacturer's instructions at 30 gm/l, and autoclaved at 121° C. for 15 minutes. Liquid culture is grown overnight in a shaking incubator at 37° C. To change solutions the cells are centrifuged at 13,000 rpm for 20 minutes, the supernatant is discarded, and the cells are resuspended in the new reagent (described below) using a vortex mixer. This washes ions and biomaterials off the cells and leaves them suspended in a small volume of distilled water. The sequence of reagents is (a) 1 ml of distilled water-repellet, (b) 1 ml of distilled water-resuspend, (c) deposit 250 μl on a clean brass specimen plate, (d) dry overnight at 30° C., (e) coat just before microscopy with 2 nm of chromium metal deposited in a Xenosput clean vacuum sputter coater. The coated specimens are examined using an Hitachi S-900 Field Emission Scanning Electron microscope using a beam energy of 3 kilovolts (University of New South Wales, NSW, Australia). Digital images at different magnifications are recorded using an ImageSlave digitizer.

The results show (representative images of *S. typhimurium* minCDE-strain are shown in FIGS. 2A-D) that parent bacterial cells range in length from 0.9 um to 4 μm and 0.4 μm to 0.5 μm in width. Following filtration steps outlined on the left side of FIG. 1, some batches show residual bacterial contamination. The contaminating bacteria are small in size, i.e., about 0.9 um in length. This indicates that some small sized bacteria that are approximately the same width as minicells (FIG. 2A) leak through the 0.45 µm cross-flow and dead-end filters.

Example 2

Elimination of Small Bacteria: Conversion Into Bacterial Filaments

This Example demonstrates that inducing bacteria to filament prior to filtration improves minicell purification processes.

A study is designed to address the problem described in Example 1, by making the residual small-sized parent bacteria substantially larger than the 0.45 µm pore size of a dead-end filter. Stress-inducing conditions in a bacterial growth environment can prevent complete septation during bacterial cell division, resulting in bacterial filaments.

The study demonstrates that hypertonic bacterial growth media (stress-inducer) reliably induce filamentation of minicell-producing bacterial strains of *S. typhimurium* and *E. coli*. All bacteria are grown from glycerol stocks maintained at −80° C. *S. typhimurium* and *E. coli* strains are grown in Trypticase Soy Broth (TSB) (BBL brand purchased from Bacto Labs, Liverpool, NSW, Australia). It is prepared according to the manufacturer's instructions at 30 gm/l, and autoclaved at 121° C. for 15 minutes. Liquid culture is grown in a shaking incubator at 37° C. Overnight bacterial culture is diluted 1:5,000 in fresh TSB and grown until $OD_{600nm}$ reaches 0.2. The culture is divided into ten 5 ml aliquots in sterile vials, and pre-autoclaved sterile NaCl is added to each vial to yield final NaCl concentrations (w/v) of 0% (control), 2%, 3%, 4.5%, 5%, 5.5%, 6%, 7% and 8%. The cultures are incubated statically at 37° C. and samples are obtained at 2 hrs, 4 hrs, 8 hrs and 24 hrs. A zero hour control sample is also obtained for microscopy. The samples are centrifuged at 13,200 rpm and the bacterial/minicell pellets are resuspended in distilled water. A drop of each sample is placed on a glass slide, air dried and heat fixed. Each sample is Gram-stained using a 95% alcohol wash followed by Gram Safranin flood for 1 min. and a water wash. The slides are visualized using the Leica Model DMLB light microscope with image analysis by means of a Leica DC camera and Leica IM image management software. Samples are viewed at 40× or oil immersion at 100× magnification.

The above-experiments are repeated four times to determine reliability of results and variations with a series of controls also are performed.

Figure 3B:
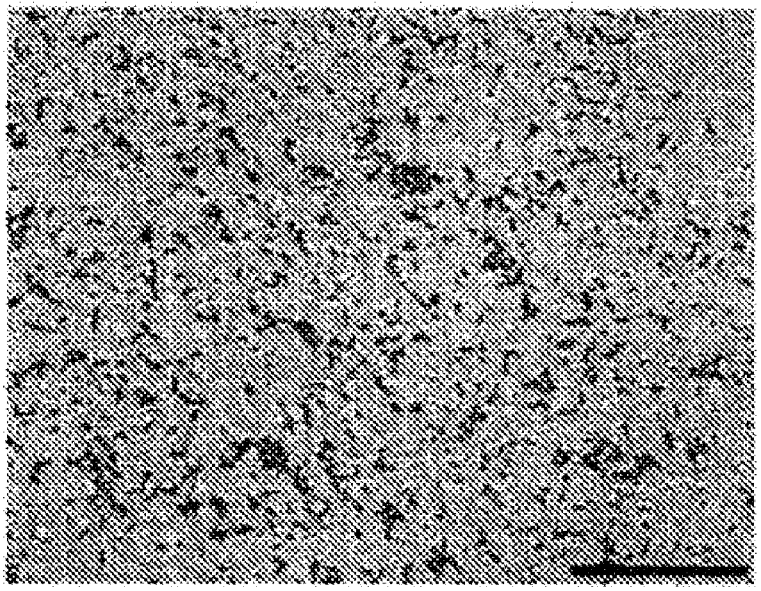
FIG. 3B shows fluorescence microscope images comparing the sizes of S. typhimurium minCDE-strain bacteria incubated in growth media for 4 hrs in the absence of NaCl (left side image) and of bacterial filaments formed after 4 hrs incubation in the presence of 5% NaCl (right side image).
Figure 3B:
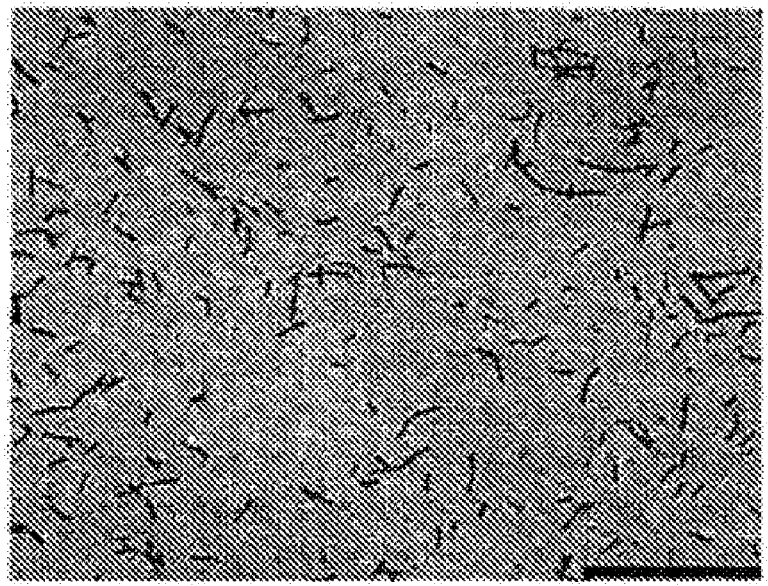
Figure 4B:
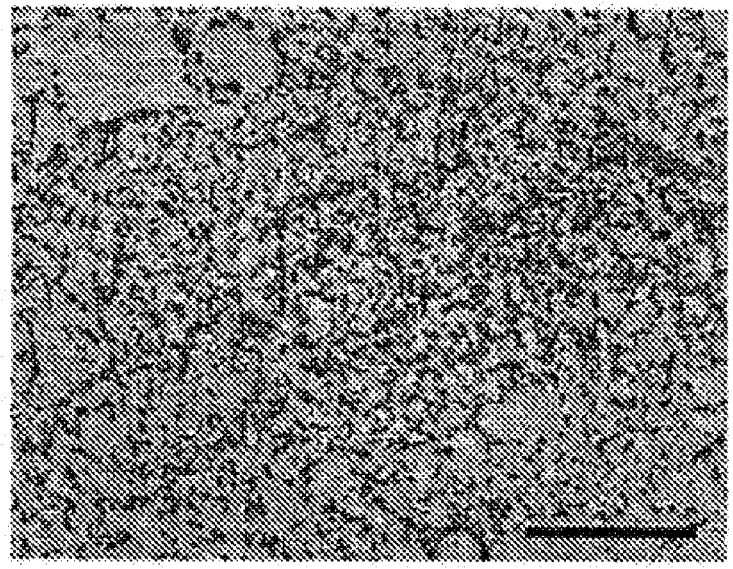
FIG. 4B shows fluorescence microscope images comparing the sizes of E. coli minCDE-strain bacteria incubated in growth media for 4 hrs in the absence of NaCl (left side image) and of bacterial filaments formed after 4 hrs incubation in the presence of 5% NaCl (right side image).
Figure 4B:
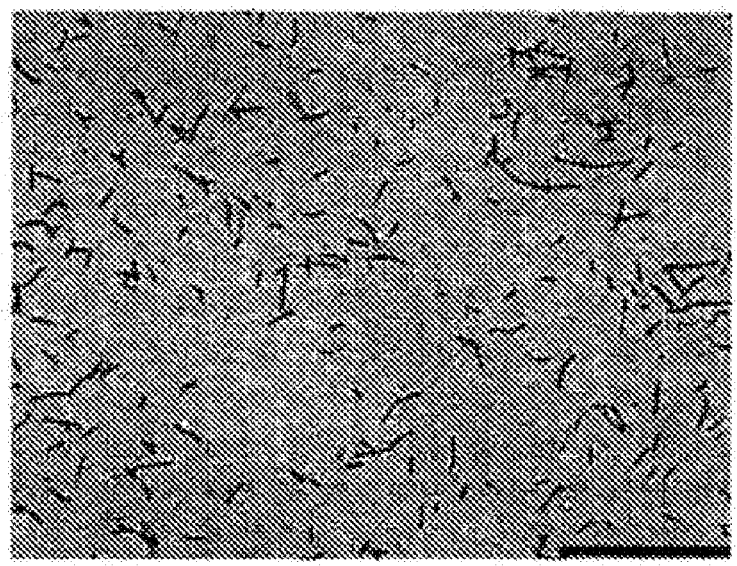

The results show (FIGS. 3A-B and 4A-B) that with increasing NaCl concentration, the bacterial cells form filaments comprising two to twenty coccobacilli stuck end-to-end. Within the range of 2% to 3% NaCl concentrations, filamentation is variable (FIGS. 3A and 4A), because several bacterial cells do not form filaments even after longer incubation periods. However, at 4% to 5% NaCl, the bacterial cells reliably turn into filaments (FIGS. 3B and 4B). The optimum incubation period for filamentation at 4% to 5% NaCl is about 4 hrs, and further incubation up to 24 hrs is not generally necessary. Higher salt concentrations of 5.5% to 8% decrease filament formation. Preliminary studies to determine a viable bacterial count of each sample by dilution plating on TSB agar plates suggests that significant numbers of bacterial cells are killed at higher salt concentrations (5.5% to 8% NaCl), a potential reason why decreased filamentation is observed at these NaCl concentrations.

A definitive study of the effect of the various NaCl concentrations on the bacterial cell viability is performed out using the LIVE/DEAD BacLight Bacterial Viability Kit (Molecular Probes, Eugene, Oreg., USA). The kit employs two nucleic acid stains, the green-fluorescent SYTO® 9 stain and the red-fluorescent propidium iodide stain. These stains differ in their ability to penetrate healthy bacterial cells. SYTO 9 stain labels both live and dead bacteria. In contrast, propidium iodide (PI) penetrates only bacteria with damaged membranes, reducing SYTO 9 fluorescence when both dyes are present. Thus, live bacteria with intact membranes fluoresce green, while dead bacteria with damaged membranes fluoresce red. The above-described experiment on salt-induced filamentation is repeated, and 0 hr, 2 hr, 4 hr, 8 hr and 24 hr samples for the various NaCl concentrations are obtained. The samples are centrifuged at 13,200 rpm, supernatant discarded and bacterial/minicell pellet is resuspended in 100 µl of BSG. 0.5 µl of a 50/50 mix of SYTO 9/PI is added to each sample and incubated for 15 min. The samples are centrifuged at 13,200 rpm, supernatant discarded and pellets are resuspended in 100 µl of distilled water. A drop of each sample is placed on a glass slide, air dried and covered with a drop of BacLight Mounting Oil. Each sample is visualized using the Leica Model DMLB light microscope with image analysis by means of a Leica DC camera and Leica digital image acquisition software. Samples are viewed at 40× or oil immersion at 100× magnification.

The results show (color photos not shown) that at NaCl concentrations of 5.5% and higher, significant numbers of bacterial cells fluoresce red (dead cells) and at NaCl concentrations of 7% and 8%, almost all of the bacterial cells are dead within 2 hrs of incubation. This result shows that 4% to 5% NaCl for an incubation time of 4 hrs is the maximum limit to achieve filamentation. After 2 hrs of incubation, the live bacterial cells turn into filaments. However as the incubation time increases the filaments fluoresce red, suggesting that even 4% to 5% NaCl is sufficient stress for the bacterial cells and that they begin to die after a few generations of growth. Since this stress appears to inhibit complete septation during bacterial cell division, it is sufficient to permit the formation of bacterial filaments. This data also explains why filamentation is not achieved at higher salt concentration: the stress is toxic, inhibiting bacterial growth and cell division, and causing cell death.

CITED PUBLICATIONS

Brahmbhatt, "Cloning and molecular characterization of the rfb gene cluster of *Salmonella typhimurium*," Ph.D. Thesis, University of Adelaide, Australia (1987).

Britton et al., "Characterization of a prokaryotic SMC protein involved in chromosome partitioning," *Genes Dev.* 12: 1254 (1998).

Clark-Curtiss & Curtiss, "Analysis of recombinant DNA using *Escherichia coli* minicells," *Methods Enzymol.* 101: 347 (1983).

de Boer et al., "Roles of MinC and MinD in the site-specific septation block mediated by the MinCDE system of *Escherichia coli*," *J. Bacteriol.* 174: 63 (1992).

Dorward et al., "Export and intercellular transfer of DNA via membrane blebs of *Neisseria gonorrhoeae*," *J. Bacteriol.* 171: 2499 (1989).

Forbes, "Crossflow microfiltration," *Australian J. Biotechnology* 1: 30 (1987).

Frazer & Curtiss, "Production, properties and utility of bacterial minicells," *Curr Top Microbiol. Immunol.* 69: 1 (1975).

Harlow et al., "Cloning and characterization of the gsk gene encoding guanosine kinase of *Escherichia coli*," *J. Bacteriol.* 177: 2236 (1995).

Harry, "Bacterial cell division: Regulating Z-ring formation," *Mol. Microbiol.* 40: 795 (2001).

Hiraga et al., "Chromosome partitioning in *Escherichia coli*: novel mutants producing anucleate cells," *J. Bacteriol.* 171: 1496 (1989).

Hu & Lutkenhaus, "Topological regulation of cell division in *Escherichia coli* involves rapid pole to pole oscillation of the division inhibitor MinC under the control of MinD and MinE," *Mol. Microbiol.* 34: 82 (1999).

Ireton et al., "spo0J is required for normal chromosome segregation as well as the initiation of sporulation in *Bacillus subtilis*," *J. Bacteriol.* 176: 5320 (1994).

Katsui et al., "Heat-induced blebbing and vesiculation of the outer membrane of *Escherichia coli*," *J. Bacteriol.* 151: 1523 (1982).

Kihara et al., "Analysis of a FliM-FliN flagellar switch fusion mutant of *Salmonella typhimurium*," *J. Bacteriol.* 178: 4582 (1996).

Levin et al., "Identification of *Bacillus subtilis* genes for septum placement and shape determination," *J. Bacteriol.* 174: 6717 (1992).

Matsuzaki et al., "Interactions of an antimicrobial peptide, magainin 2, with outer and inner membranes of Gram-negative bacteria," *Biochim Biophys. Acta.* 1327: 119 (1997).

Okada et al., "Possible function of the cytoplasmic axial filaments in chromosomal segregation and cellular division of *Escherichia coli*," *Sci. Prog.* 77: 253 (1993-94).

Okada et al., "Cytoplasmic axial filaments in *Escherichia coli* cells: possible function in the mechanism of chromosome segregation and cell division," *J. Bacteriol.* 176: 917 (1994).

PCT/IB02/04632, Intact minicells as vectors for DNA transfer and gene therapy in vitro and in vivo.

Raskin & de Boer, "MinDE-dependent pole-to-pole oscillation of division inhibitor MinC in *Escherichia coli*," *J. Bacteriol.* 181: 6419 (1999).

Reeve, "Use of minicells for bacteriophage-directed polypeptide synthesis," *Methods Enzymol.* 68: 493 (1979).

Reeve & Cornett, "Bacteriophage SPO1-induced macromolecular synthesis in minicells of *Bacillus subtilis*," *J. Virol.* 15: 1308 (1975).

Sancar et al., "Simple method for identification of plasmid-coded proteins," *J. Bacteriol.* 137: 692 (1979).

Stewart & D'Ari, "Genetic and morphological characterization of an *Escherichia coli* chromosome segregation mutant," *J. Bacteriol.* 174: 4513 (1992).

Wachi et al., "New mre genes mreC and mreD, responsible for formation of the rod shape of *Escherichia coli* cells," *J. Bacteriol.* 171: 6511 (1989).

What is claimed is:

1. A pharmaceutical composition consisting essentially of (A) a biologically compatible medium that is isotonic and non-toxic and (B) intact bacterial minicells wherein said bacterial minicells are derived from *S. typhimurium* or *E. coli*, are approximately 0.4 μm in diameter, and are purified from parent bacterial cells in a sample enriched for minicells by a process that comprises filtering said sample with (a) at least one filter having a pore size of about 0.45 μm, such that minicells but not bacterial cells pass, and (b) at least one filter having a pore size of less than or equal to 0.2 μm, wherein said composition (i) contains fewer than about 1 contaminating parent bacterial cell per $10^9$ minicells and (ii) is substantially free of cellular debris and endotoxin.

2. The composition of claim 1, wherein said preparation contains fewer than about 1 contaminating parent bacterial cell per $10^{10}$ minicells.

3. The composition of claim 1, wherein said preparation contains fewer than about 1 contaminating parent bacterial cell per $10^{11}$ minicells.

4. The composition of claim 1, wherein said a process further comprises subjecting a sample containing minicells to density gradient centrifugation in a biologically compatible medium.

5. The composition of claim 4, wherein said process further comprises a preliminary step of performing differential centrifugation on said sample containing minicells.

6. The composition of claim 1, wherein either of said filtering steps comprises a serial filtration process that combines cross-flow filtration and dead-end filtration.

7. The composition of claim 1, wherein said process further comprises inducing parent bacterial cells to adopt a filamentous form.

8. The composition of claim 7, wherein said process further comprises treating said preparation with an antibiotic.

9. The composition of claim 8, wherein said process further comprises exposing said preparation to magnetic beads coated with anti-lipid A antibody.

10. The composition of claim 1, wherein either of said filtering steps comprises a serial filtration process that combines cross-flow filtration and dead-end filtration and said process further comprises inducing parent bacterial cells to adopt a filamentous form.

11. The composition of claim 10, wherein said process further comprises treating said preparation with an antibiotic.

12. The composition of claim 11, wherein said process further comprises exposing said preparation to magnetic beads coated with anti-lipid A antibody.

13. The composition of claim 1, wherein said composition comprises at least $10^{10}$ minicells.

* * * * *